United States Patent [19]
Tsao et al.

[11] Patent Number: 5,611,464
[45] Date of Patent: Mar. 18, 1997

[54] CONTAINER FOR PRESERVING MEDIA IN THE TIP OF A SOLUTION DISPENSER

[75] Inventors: Fu-Pao Tsao, Lawrenceville; Stephen M. Martin, Roswell; Harold Shlevin, Marietta; Thomas E. Rowe, Roswell, all of Ga.

[73] Assignee: CIBA Geigy Corporation, Tarrytown, N.Y.

[21] Appl. No.: 449,476

[22] Filed: May 30, 1995

[51] Int. Cl.⁶ ..................................................... B67D 5/58
[52] U.S. Cl. ................... 222/189.06; 222/190; 222/212; 222/420; 604/295
[58] Field of Search ..................................... 222/190, 212, 222/420, 502, 566, 189.06; 604/295

[56] References Cited

U.S. PATENT DOCUMENTS

| | | | |
|---|---|---|---|
| 4,812,173 | 3/1989 | Tsao et al. | 134/27 |
| 4,889,689 | 12/1989 | Tsao | 422/30 |
| 5,056,689 | 10/1991 | Heyl et al. | 222/189 |
| 5,080,800 | 1/1992 | Heyl et al. | 210/679 |

FOREIGN PATENT DOCUMENTS

| | | |
|---|---|---|
| 0196075 | 3/1986 | European Pat. Off. . |
| 0354186 | 7/1989 | European Pat. Off. . |
| 0542686 | 4/1992 | European Pat. Off. . |
| 0567431 | 4/1993 | European Pat. Off. . |
| WO9204004 | 3/1992 | WIPO . |
| WO9317720 | 9/1993 | WIPO . |

*Primary Examiner*—James J. Seidleck
*Assistant Examiner*—John M. Cooney, Jr.
*Attorney, Agent, or Firm*—Edward McC. Roberts; R. Scott Meece; Michael U. Lee

[57] ABSTRACT

A container, composition and method for preserving treatment solutions, in which the composition includes weak and strong preservatives. The dispensing container includes media within a dispensing tip which media removes or alters the strong preservative, while allowing the weak preservative to inhibit microbial growth in the tip media. The dispensing container is especially useful in delivering to the ocular environment ophthalmic solutions which are essentially free of strong preservative which may cause patient discomfort. A dispensing container including a pH-preserved pilocarpine solution is disclosed in one embodiment.

13 Claims, 1 Drawing Sheet

CONTAINER FOR PRESERVING MEDIA IN THE TIP OF A SOLUTION DISPENSER

BACKGROUND OF THE INVENTION

1. Field of the invention

This invention relates broadly to containers for handling solutions which must be maintained essentially free of microbial growth and to methods of preserving such containers and solutions. More particularly, the invention relates to ophthalmic dispensers and preserved ophthalmic solutions.

2. Description of the Related Art

Various contact lens care solutions for improving consumer comfort and safety are currently being marketed. Examples include wetting solutions to enhance the lens compatibility with the eye; storage solutions which prevent lens dehydration, microbial contamination, or optical distortion; and cleaning solutions which remove lipids, proteins, or other biological matter attached to the lens surface. In addition, there are numerous ophthalmic solutions designed to reduce ocular discomfort, treat ocular illnesses, or enhance ocular wound healing (e.g., subsequent to surgery). Many of these lens care solutions and ophthalmic treatment solutions, both referred to herein as ophthalmic solutions, are provided to the consumer in plastic containers or aerosol cans having a nozzle or tip through which the solution is dispensed.

Many ophthalmic solutions are dispensed directly into the eye of the consumer, and the tip of the dispenser may contact ocular tissue or fluids. Thus, microbes or ocular pathogens may contaminate the ophthalmic dispenser, and over extended storage times, may increase to concentrations which may threaten the consumer's health or comfort when the ophthalmic solution is introduced into the eye. Solution contamination may also occur by merely exposing the solution to the surrounding air, which exposure may occur when a consumer dispenses the solution. Accordingly, ophthalmic solutions typically include a preservative or antimicrobial, such as polymyxin B sulfate, quaternary ammonium compounds, chlorobutanol, organic mercurials, p-hydroxybenzoic acid esters, certain phenols or substituted alcohols.

A different type of preservative is required in solutions which include an active agent or drug which is unstable under certain conditions. For example, pilocarpine is known to be unstable at basic pH levels. In order to prevent degradation of the active agent, preservatives may be added to the solution. In the case of pilocarpine, preservative acids or buffers may be added to prevent degradation.

The use of such preservatives in ophthalmic solutions is problematic because the preservatives may cause irritation when they contact ocular tissues. For example, benzalkonium chloride (BAK) is known to be a useful ophthalmic preservative, and has broad antibacterial and antifungal activity in combination with other additives, such as disodium ethylene diaminetetraacetic acid (EDTA). However, BAK may denature corneal protein, causing eye damage and discomfort. Further, some consumers have allergic reactions to some preservatives, such as BAK, even at relatively low concentrations.

U.S. Pat. Nos. 5,056,689 and 5,080,800, both issued on application of Heyl, et al., disclose a remarkably innovative solution to the aforementioned ophthalmic preservative problem. These patents teach the use of a "scavenger" material in the tip of the ophthalmic dispenser. As the solution is dispensed through the scavenger-containing tip, the preservative is removed from the solution. Depending on the preservative used, the scavenger may "remove" preservative by a chemical reaction which neutralizes the preservative, by ion exchange, by adsorption, by absorption, and the like. Thus, the solution which is dispensed from the tip into the consumer's eye is virtually preservative-free, thereby avoiding or minimizing any of the previously described problems associated with the preservative's contacting ocular tissue. Advantageously, the ophthalmic solution within the container remains microbe-free, because preservative within the solution inhibits microbial growth.

However, a problem which may arise with the Heyl, et al. invention is that the scavenger media itself may not be sufficiently preserved. While preservative inhibits microbial growth in the ophthalmic solution within the container, the preservative has been removed from the scavenger media and any ophthalmic solution remaining on the scavenger media. Thus, microbes contaminating the tip media may be allowed to propagate, thereby increasing concentrations to unacceptable levels.

Hence, there is a need for a method of preserving scavenger media within the tip of an ophthalmic dispenser, without causing introduction of unacceptable levels of preservative into the eye during dispensing. Analogously, there is a need for an ophthalmic dispenser having a scavenger tip which is itself preserved.

SUMMARY OF THE INVENTION

An object of the present invention is to provide a preserved-solution-dispensing system capable of dispensing solutions essentially free of preservatives which irritate or damage target tissues.

Another object of the invention is to provide a method of preserving both solutions and scavenger media in medicinal solution dispensers.

One embodiment of the invention is a method of preserving a composition in a container. The method involves placing a composition including a weak preservative and a strong preservative within a container. The method also includes providing the container with a dispensing tip through which the composition may be dispensed. The dispensing tip includes media which will remove the strong preservative from the composition upon dispensing the composition through the media, but which will not completely remove the weak preservative. The weak preservative inhibits microbial growth in the tip media, while the strong preservative prevents microbial growth and kills microbes present in the composition while in the container.

Another embodiment of the invention is a container including a preserved composition. The container defines a reservoir which retains the composition. The container includes a dispensing tip through which a composition may be dispensed. The composition includes a strong preservative to kill microbes in the composition and a weak preservative to inhibit microbial growth in the media. In operation, the composition is dispensed through the tip media, which removes the strong preservative, while leaving a sufficient amount of weak preservative to inhibit microbial growth in the media. Thus, the composition exiting the tip contains only a weak preservative, which is insufficient to cause substantial discomfort to a patient applying the composition to a sensitive bodily area.

Yet another embodiment of the invention is a preserved ophthalmic composition including at least one active agent, 0.0004 to 0.1 weight percent weak preservative, and 0.00005 to 0.2 weight percent strong preservative. The preferred weak preservative is sodium perborate. A particularly preferred composition includes 0.1 to 10 weight percent pilocarpine preserved at a pH of 2 to 7.

DESCRIPTION OF THE PREFERRED EMBODIMENTS

Figure 1:
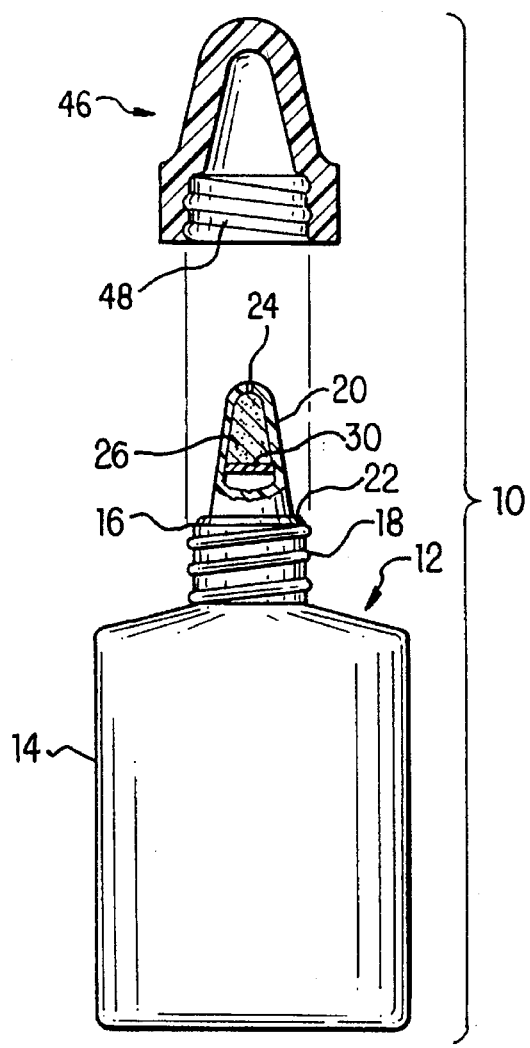
FIG. 1 is an exploded view of a first embodiment of the present invention in which scavenging material is provided within a dispensing container.

One embodiment of the present invention is a dispensing system including a container which retains a solution including a weak preservative and a strong preservative, and which container has a dispensing portion or tip having a means for removing the strong preservative from the solution without removing the weak preservative therefrom. The means for removing the strong preservative is termed "scavenging media" or "media" herein, and refers to any and all materials which will remove the strong preservative from solution or alter the nature of the strong preservative to minimize or inhibit irritation, damage or other detrimental effect to the target application area. "Removal of strong preservative", as used herein, refers to neutralization of the preservative with a chemical reaction (e.g., pH modification), ion exchange, adsorption, absorption, and the like. While the invention has particular utility in the ophthalmic field, the invention has utility in the preservation of a wide variety of treatment (e.g., medicinal) solutions.

The strong preservative may be selected (1) to both inhibit microbial growth and kill microorganisms which inadvertently contaminate the ophthalmic solution upon exposure to the surroundings or (2) to inhibit the degradation or deactivation of the active agent. The strong preservative may be selected from a variety of well known preservatives, including hydrophobic or non-charged preservatives, anionic preservatives, and cationic preservatives. The strong preservative may also be an acid, base, or buffer, selected to maintain the composition at a pH which prevents degradation of the active agent. For example, an acid or buffer is preferred to prevent pilocarpine degradation.

Strong cationic preservatives include, without limitation thereto, polymyxin B sulfate, quaternary ammonium compounds, poly(quaternary ammonium) compounds, p-hydroxybenzoic acid esters, certain phenols and substituted alcohols, benzalkonium chloride, cetylpridinium chloride, benzethonium chloride, cetyltrimethyl ammonium bromide, chlorhexidine, poly(hexamethylene biguanide), and mixtures thereof. Poly(quaternary ammonium) compounds include BUSAN 77, ONAMER M, MIRAPOL A15, IONENES A, POLYQUATERNIUM 11, POLYQUATERNIUM 7, BRADOSOL, AND POLYQUAT D-17-1742. A preferred preservative for the ophthalmic field is benzalkonium chloride.

Strong anionic preservatives include, without limitation thereto, 1-octane sulfonic acid (monosodium salt); 9-octadecenoic acid (sulfonated); ciprofloxacin; dodecyl diphenyloxide-disulfonic acid; ammonium, potassium, or sodium salts of dodecyl benzene sulfonic acid; sodium salts of fatty acids or tall oil; naphthalene sulfonic acid; sodium salts of sulfonated oleic acid; organic mercurials such as thimerosal (sodium ethylmercurithiosalicylate); thimerfonate sodium (sodium p-ethylmercurithiophenylsulfonate).

Strong hydrophobic or non-ionic preservatives include, without limitation thereto, 2,3-dichloro-1,4-naphthoquinone; 3-methyl-4-chlorophenol (PREVENTOL CMK); 8-hydroxyquinoline and derivatives thereof; benzyl alcohol; bis(hydroxyphenyl) alkanes; bisphenols; chlorobutanol; chloroxylenol; dichlorophen [2,2'-methylene-bis(4-chlorophenol)] (PANACIDE); ortho-alkyl derivatives of para-bromophenol and para-chlorophenol; oxyquinoline; para-alkyl derivatives of ortho-chlorophenol and ortho-bromophenol; pentachlorophenyl laurate (MYSTOX LPL); phenolic derivatives such as 2-phenylphenol, 2-benzyl-4-chlorophenol, 2-cyclopentyl-4-chlorophenol, 4-t-amylphenol, 4-t-butylphenol, and 4-and 6-chloro-2-pentylphenol; phenoxy fatty acid polyester (PREVENTOL B2); phenoxyethanol; and phenylethyl alcohol.

In one embodiment, the strong preservative is present in the solution in an amount sufficient to kill microbes which inadvertently enter the dispensing container over the period of use. The desirable concentration will depend on a number of factors, including the strength of the preservative, the conditions of dispenser use, and the length of time the dispenser and solution will be in service. Generally, the strong preservative may be present in a concentration from about 0.00005 to about 0.2 weight percent, and more preferably the concentration is about 0.005 to about 0.2 weight percent.

The weak preservative is selected to merely inhibit microbial growth in the media which removes the strong preservative. The weak preservative may also be important in inhibiting microbial growth within the solution, not merely within the media, in cases where the strong preservative is selected solely to stabilize the active agent. The weak preservative, at the concentrations of use, should not be sufficiently potent to cause irritation of the target tissue which the solution will contact, because the weak preservative will not be removed from the solution by the media which removes the strong preservative. Examples of weak preservatives useful in accordance with the present invention include, without limitation thereto, peroxides, such as hydrogen peroxide; peroxide-generating species, such as an alkali perborate or a combination of sodium perborate, boric acid, and sodium borate; urea peroxide; sodium peroxide carbonate; sodium persulfate; sodium perphosphate; and poly(vinyl pyrrolidone) hydrogen peroxide. A preferred weak preservative is sodium perborate. The amount of weak preservative in solution is preferably about 0.004 to 0.1 weight percent, more preferably about 0.001 to 0.02 weight percent.

In dispensing systems which include a peroxide or peroxide-generating species such as sodium perborate, the solution preferably includes a component which inhibits peroxide decomposition, i.e., a peroxide stabilizer. A wide variety of ophthalmically-compatible peroxide stabilizers may be used, including sodium stannate. Other highly useful peroxide stabilizers include hydroxyethylidene diphosphonic acid (e.g., DEQUEST 2010) with glycerol and diethylene triamine penta(methylenephosphonic acid) (e.g., DEQUEST 2060), as disclosed more fully in U.S. Pat. Nos. 4,812,173 and 4,889,689, respectively, which are incorporated herein by reference.

Figure 2:
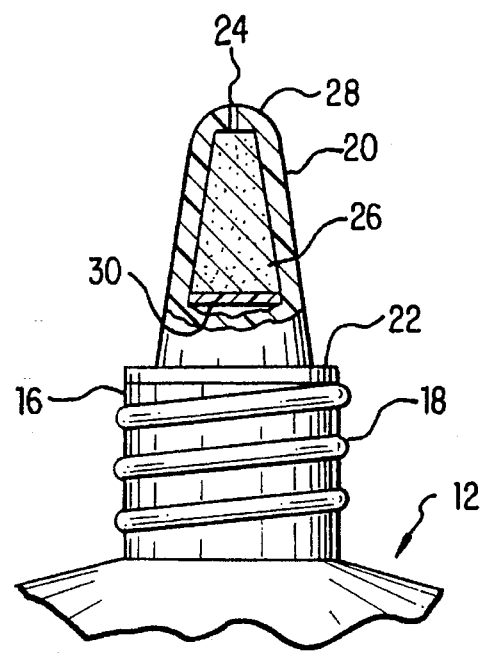
FIG. 2 is a partial sectional view of a first embodiment of the present invention in which scavenging material is provided within a dispensing container.

The dispensing system structure may be understood more readily with reference to the Figures. Referring to FIG. 1, a preserved device 10 for removing preservatives from solutions, such as ophthalmic solutions, is shown. Device 10 includes container 12, preferably constructed of molded plastic, having resilient sidewalls 14 which define a solution-retaining chamber. Resilient sidewalls 14 preferably may be deformed by inward pressure (e.g., manual squeezing by a consumer) to produce an internal container pressure capable of causing solution to be dispensed through dispensing head 20. Container 12 is provided with an upstanding neck portion 16 having external threads 18 thereabout. Dispensing head 20 is provided atop neck portion 16, either integrally as shown in FIGS. 1–2 by threading engagement, or by snap-fitting engagement or other equivalent affixation means. Flange portion 22 is provided between dispensing head 20 and container neck 16. Dispensing head 20 has a passageway extending through the length of head 20, which in turn, has a first end in fluid communication with the chamber and a second end, container outlet 24, in fluid communication with the surroundings.

In one embodiment of the present invention, as shown in FIGS. 1 and 2, means for removing strong preservatives are placed directly with dispenser head 20. In a preferred embodiment, preservative-removing means comprise scavenging media 26, provided between the chamber and the container outlet 24, in the path of the solution as the solution is dispensed from container 12. Scavenging media 26 is preferably positioned as close as possible to outlet 24 to minimize dead space in the upper portion of dispensing head 20. Media 26 may be compressed into a porous mass which is preferably insert-molded into dispensing head 20. However, a variety of other means of maintaining the material in the path of the solution (e.g., mechanical retention such as fine mesh screen) may be used. Alternatively, as shown in FIG. 2, media 26 may be in the form of fine particles, held in place by porous supporting members 28 and 30. Members 28 and 30 may be made from porous plastic, such as porous polyethylene or polypropylene. In either case, the solution must be able to pass through the scavenging media 26 as it exits container 12, in order to remove the strong preservative.

A variety of other dispenser designs are useful in accordance with the present invention. For example, a fitment including scavenger media may be provided separate from the dispensing container, so that the fitment is affixed to the container outlet before use. Also, a uni-directional valve (i.e., a check valve) may be provided on the container outlet to minimize the likelihood of contamination. Furthermore, a separate inlet means may be provided for allowing air to return to the container after the container has been squeezed to dispense solution. Other embodiments of dispensing containers and associated components may be found in U.S. Pat. Nos. 5,056,689 and 5,080,800, which are hereby incorporated by reference.

A wide variety of scavenging media may be used to remove the strong preservative. For example, removal of the strong preservative can be accomplished by ion-exchange or chemical-affinity mechanisms, such as with fumed silica. The choice of the scavenger media depends on the character of the strong preservative. Thus, scavenger media 26 may be an anionic medium for removing cationic strong preservatives, a cationic medium for removing anionic strong preservatives, or a hydrophobic or non-ionic medium for removal of hydrophobic or non-ionic preservatives. Other scavenging media useful in the present invention are those relating to chemical-affinity techniques, such as immunoassay, active site binding and affinity chromatography.

Scavenging media 26 for removing positively charged (cationic) strong preservatives, including hydrogen ions, is preferably an inert material having negative charges or a partially negatively-charged material, such that the positively charged (e.g., quaternary ammonium) compound adheres to media 26 as it flows through dispensing head 20. Negatively charged (anionic) media include, without limitation thereto, poly(hydroxymethacrylate). Examples of products capable of removing positively charged preservatives, such as benzalkonium chloride, include, without limitation thereto, AG-50X8, AG-50X16, BIO-BX-SM2, and BIOREX70, all available from BIO-RAD Laboratories, Richmond, Calif.; DOWEX 50X2, 50X4, 50X8, and 50X16, all available from Dow Chemical Company; and ACROPOR 5A-6404, available from Gelman Sciences, Ann Arbor, Mich.

Hydrophobic (non-ionic) scavenger media may be used to remove strong hydrophobic preservatives. Examples of hydrophobic media include, without limitation thereto, non-ionic polymeric adsorbents such as AMBERLITE XAD-2, XAD-4, XAD-7, and XAD-8; activated carbon adsorbents; molecular sieves; magnesium silicate; silica gel; poly(vinyl pyrrolidone) and activated aluminum oxide.

Negatively charged components, may be removed by using positively charged scavenger media 26. Examples of positively charged (cationic) scavenger media include BIO-REX 5, AG-1, AG-2, AG-10 and AG-MP-1 from BIO-RAD Laboratories; AMBERLITE IRA; DOWEX 1 and 2; and DIAION anionic ion-exchange media. For example, CHELEX 100 from BIO-RAD will remove thimerosal from solution.

Alternatively, the scavenging material may be a porous plastic, such as porous polyethylene, imbedded with a cross-linked styrene divinyl benzene which is sulfonated to produce either a positively-charged hydrogen form or a negatively-charged sodium form.

For example, it has been found that a scavenging material composed of a mixture of "Bio Rex 5" and "AG-4", both Bio Rad products, in a 75 to 25 ratio, will almost completely remove 0.1% sorbic acid from a solution and raise the pH of the solution from 4.0 to 7.0. This is relevant since sorbic acid is commonly used as a preservative in contact lens care solutions. Also, sorbic acid is normally stored at a pH of 7.0, where it is not stable. At a pH of 4.0, it is stable but cannot be instilled into the eye. The present invention will therefore allow solution to be stored at low pH, and subsequently administered at a higher ocularly-acceptable pH, while maintaining the dispenser, especially the scavenger media, in a preserved state.

The pharmaceutic agents which may be ophthalmically delivered in accordance with the present invention are varied. The term "pharmaceutical agent", as used herein, refers broadly to a class of agents which are desirable to deliver via a solution or suspension. "Pharmaceutical agents" include, but are not limited to, beneficial therapeutic drugs (especially ophthalmic agents), diagnostic agents, vitamins, nutrients, and the like. While a wide variety of pharmaceutical agents may be used in accordance with the present invention, the pharmaceutical agent must be compatible with both the preservative and the ion exchange media. Examples of pharmaceutical agents which may be delivered in accordance with the present invention include, without limitation thereto, atropine, betaxolol, cyclopentolate, dichlorphenamide, diclofenac, flurbiprofen, homatropine, hydroxyamphetamine, idoxuridine, isoflurophate, levobunolol, levocabastine, lidocaine, mefenamic acid, oxymetazoline, physotigmine, pilocarpine, procaine, scopolamine, tetrahydrozoline, trifluridine, tropicamide, vidarabine, and pharmacologically acceptable salts thereof.

In a preferred embodiment, a pilocarpine solution is prepared for delivery to the ocular environment. Pilocarpine is susceptible to degradation at ocularly-acceptable pH levels. Thus, the pilocarpine solution is maintained at a pH of about 3.5 to 7.0, more preferably 3.5 to 6.5, while in the dispensing container. The amount of pilocarpine in solution is preferably about 0.1 to 10 weight percent, more preferably about 0.1 to 4 weight percent. A strong preservative is present in an amount sufficient to kill microbes which inadvertently enter the dispensing container. Preferably, the pilocarpine solution includes 0.005 to 0.02 weight percent benzalkonium chloride. In order to remove the benzalkonium chloride, a cationic scavenger media including one or more of the following commercial products is used: AMBERLITE IRP 64, AMBERLITE IRP 69, or AMBERLITE 200 (all available from Rohm-Haas), IONAC C-249, IONAC MACRO-CAT, or AG-50W (available from BIO-RAD). In addition, the dispensing tip includes media capable of raising the pH to an ocularly acceptable level for direct application of solution into the eye. A weak preservative, as discussed above, is included to inhibit microbial growth in the scavenger media.

In addition, a peroxide stabilizer is preferably added in an amount sufficient to stabilize the peroxide over the period of use of the dispenser. Examples of peroxide stabilizers include, without limitation thereto, diethylene triamine penta(methylene phosphonic acid), 1-hydroxyethylidene-1,1-diphosphonic acid, and physiologically compatible salts thereof. A preferred peroxide stabilizer which is commercially available is DEQUEST 2060 (available from Monsanto). While the preferred amount of peroxide stabilizer depends on a variety of factors, generally about 0.002 to 0.2 weight percent peroxide stabilizer may be added to the solution. A more preferred range of peroxide stabilizer is about 0.005 to 0.03 weight percent.

The previous disclosure will enable one having ordinary skill in the art to practice the invention. In order to better enable the reader to understand specific embodiments and the advantages thereof, reference to the following examples is suggested.

EXAMPLE I

An ophthalmic test solution is prepared with the following composition:

0.3 weight percent Methocel E4M (Dow Chemical Co.)

0.3 weight percent sodium chloride 0.12 weight percent potassium chloride 0.5 weight percent boric acid 0.01 weight percent benzalkonium chloride 0.006 weight percent DEQUEST 2060

0.0091 weight percent sodium perborate water q.s.

A USP antimicrobial preservative effectiveness test, described generally at page 1151 of the *U.S. Pharmacopeia*, 21st Revision (1985), is performed on the solution. The test is described briefly as follows.

Inoculum is prepared by inoculating USP test saline with about $2.0\times10^6$ CFU/ml of the following test microorganisms: *Aspergillus niger, Candida albicans, Escherichia coli, Pseudomonas aeruginosa,* and *Staphylococcus aureus.* A sterile tip filled with ion exchange media (AMBERLITE IRP-69 cationic resin) in bead form is affixed to the top of a bottle filled with test solution. One drop of test solution is dispensed through the tip. The tip is then removed from the bottle. Five tips are used for each data point for each of the five microorganism types.

About 0.5 ml of inoculum is injected through the orifice of each tip with a tuberculin syringe. The inoculated tip is placed in a sterile petri plate (5 tips per plate) and incubated in a humidified incubator at 20°–25° C. for 14 and 28-day periods.

Microorganisms are recovered from tips by the following process. First, the exterior of the tip is swabbed with 70% isopropyl alcohol. Next, the tip is held with sterile forceps while the membrane is cut back with a sterile scalpel. The tip is then inserted into 10 ml neutralizing broth ($10^{-1}$) in a 50 ml polypropylene tube and vortexed vigorously. The solution is diluted by additional neutralizing broth ($10^{-3}$) and 1 ml is plated in duplicate in an appropriate agar. The plates are incubated at 30°–35° C. for 48–72 hours for bacteria and 20°–25° C. for the same period for fungus. The colonies are counted and the number of microorganisms per tip is determined.

The preservative effectiveness test is considered passed if (1) there is a 3 log or greater reduction of the challenge bacteria at 14 days, (2) the level of fungi remains at or below inoculum level at 14 days, and (3) the concentration of each test microorganism remains at or below these designated levels during the remainder of the 28-day test period.

The pH of the solution is about 7 and osmolality is about 220 msom/kg. The tips (ion exchange resin) do not pass the preservative effectiveness test, as shown in Table I.

EXAMPLE II

An ophthalmic solution is prepared as in Example I, except that 0.0136 weight percent sodium perborate is used, instead of the lesser amount of sodium perborate of Example I. The tips pass the preservative effectiveness test, as shown in Table I.

EXAMPLE III

An ophthalmic solution is prepared as in Example I, except that 0.0181 weight percent sodium perborate is used, instead of the lesser amount of sodium perborate of Example I. The tips pass the preservative effectiveness test, as shown in Table I.

EXAMPLE IV

An ophthalmic solution is prepared as in Example I, except that 0.0226 weight percent sodium perborate is used, instead of the lesser amount of sodium perborate of Example I. The tips pass the preservative effectiveness test, as shown in Table I.

COMPARATIVE EXAMPLE V

An ophthalmic solution is prepared as in Example I, except that no sodium perborate is used. The tips do not pass the preservative effectiveness test, as shown in Table I.

TABLE 1

| EXAMPLE | WEIGHT PERCENT SODIUM PERBORATE | USP TEST |
|---|---|---|
| I | 0.0091 | fail |
| II | 0.0136 | PASS |
| III | 0.0181 | PASS |
| IV | 0.0226 | PASS |
| V | NONE | fail |

As shown in TABLE 1, the solutions including 0.0091 weight percent or less sodium perborate failed the USP antimicrobial preservative effectivenss test. However, solutions including 0.0136 to 0.0226 weight percent sodium perborate passed the test. The results illustrate that peroxide or a peroxide-generating species may be used to preserve the scavenger media in medicinal dispensing containers, especially ophthalmic dispensing containers.

The invention has been described in detail, with reference to certain preferred embodiments, in order to enable the reader to practice the invention without undue experimentation. However, a person having ordinary skill in the art will readily recognize that many of the previous components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, the intellectual property rights to this invention are defined only by the following claims and any reasonable extensions thereof.

That which is claimed is:

1. A container including a preserved composition, comprising:
    (a) a container defining a reservoir and including a dispensing tip through which a composition may be dispensed; and
    (b) a composition including:
        (1) a strong preservative, and
        (2) a weak preservative;
    wherein said dispensing tip includes a media which will inactivate or remove said strong preservative from said composition when said composition passes through said dispensing tip without completely removing said weak preservative,
    whereby said weak preservative inhibits microbial growth in said tip media, while said strong preservative inhibits microbial growth in said composition or inhibits degradation of an active agent contained in said composition.

2. A container of claim 1, wherein said strong preservative is selected from the group consisting of polymyxin B sulfate, poly(quaternary ammonium) compounds, chlorobutanol, organic mercurials, p-hydroxybenzoic acid esters, certain phenyls and substituted alcohols, benzalkonium chloride, cetylpridinium chloride, benzethonium chloride, cetyltrimethyl ammonium bromide, chlorhexidine, poly(hexamethylene biguanide), and mixtures thereof.

3. A container of claim 2, wherein said strong preservative is benzalkonium chloride.

4. A container of claim 2, wherein the concentration of said strong preservative is 0.00005 to 0.2 weight percent.

5. A container of claim 1, wherein said weak preservative is selected from the group consisting of peroxides and peroxide-generating compositions.

6. A container of claim 5, wherein said weak preservative is hydrogen peroxide.

7. A container of claim 5, wherein said weak preservative includes sodium perborate.

8. A container of claim 7, wherein said composition includes 0.004 to 0.1 weight percent sodium perborate.

9. A container of claim 5, wherein said composition includes 0.001 to 0.02 weight percent sodium perborate.

10. A container of claim 1, wherein said media is capable of altering the pH of said composition upon contacting said media with said composition.

11. A container of claim 1, wherein said composition further includes at least one pharmaceutical agent.

12. A container of claim 11, wherein said pharmaceutical agent is selected from the group consisting of atropine, betaxolol, cyclopentolate, dichlorphenamide, diclofenac, flurbiprofen, homatropine, hydroxyamphetamine, idoxuridine, isoflurophate, levobunolol, levocabastine, lidocaine, mefenamic acid, oxymetazoline, physotigmine, pilocarpine, procaine, scopolamine, tetrahydrozoline, trifluridine, tropicamide, vidarabine, and pharmacologically acceptable salts thereof.

13. A container of claim 11, wherein said pharmaceutical agent is pilocarpine and said pilocarpine is present at 0.1 to 10 weight percent.

* * * * *